United States Patent
Thomas

(10) Patent No.: US 8,714,165 B2
(45) Date of Patent: May 6, 2014

(54) DENTAL CARE DEVICE

(76) Inventor: Scott Thomas, Fairfield, CA (US)

( * ) Notice: Subject to any disclaimer, the term of this patent is extended or adjusted under 35 U.S.C. 154(b) by 0 days.

(21) Appl. No.: 12/803,595

(22) Filed: Jun. 29, 2010

(65) Prior Publication Data

US 2010/0269280 A1    Oct. 28, 2010

Related U.S. Application Data

(63) Continuation-in-part of application No. 12/316,971, filed on Dec. 17, 2008, now abandoned.

(51) Int. Cl.
*A61C 15/00* (2006.01)
*A45D 44/18* (2006.01)

(52) U.S. Cl.
USPC .......................................... 132/309; 132/323

(58) Field of Classification Search
USPC ............ 132/308, 309, 311, 323, 329; 15/22.2
See application file for complete search history.

(56) References Cited

U.S. PATENT DOCUMENTS

| | | | |
|---|---|---|---|
| 1,537,853 A | 5/1925 | Mason | |
| 1,816,092 A * | 7/1931 | Schmitter | 132/309 |
| 2,113,439 A * | 4/1938 | Bean | 132/309 |
| 2,233,936 A | 3/1941 | Campbell | |
| 2,517,806 A | 8/1950 | Streiler | |
| 2,607,358 A * | 8/1952 | Maas | 132/326 |
| D191,821 S | 11/1961 | Mitchell | |
| 3,850,182 A | 11/1974 | Clark, Jr. | |
| 3,939,853 A * | 2/1976 | Spanondis | 132/323 |
| 4,016,891 A | 4/1977 | Kupperman et al. | |
| D283,761 S | 5/1986 | Chen | |
| D290,312 S | 6/1987 | Wang | |
| 5,184,631 A * | 2/1993 | Ikeda | 132/323 |
| 5,267,579 A * | 12/1993 | Bushberger | 132/322 |
| 5,934,295 A * | 8/1999 | Gekhter et al. | 132/309 |
| D420,805 S | 2/2000 | Bahl | |
| 6,554,522 B1 * | 4/2003 | Connelly et al. | 401/272 |
| 2003/0019503 A1 | 1/2003 | Foster | |
| 2004/0040571 A1 | 3/2004 | Williams, Sr. et al. | |
| 2004/0187887 A1 | 9/2004 | Beckman | |
| 2005/0000537 A1 * | 1/2005 | Junkins | 132/309 |
| 2005/0211262 A1 | 9/2005 | Raab | |

* cited by examiner

*Primary Examiner* — Rachel Steitz
(74) *Attorney, Agent, or Firm* — Daniel Boudwin; Global Intellectual Property Agency LLC

(57) ABSTRACT

A dental care device utilizing a shaft having a proximal end portion, a distal end portion, and an intermediate portion there between. A dental brush is located on the shaft at the distal end while a wishbone support is found on the proximal end of the shaft. The wishbone support includes a gripping post and a groove which allows dental floss to extend from the post, along its outer surface, and to span the end legs of the wishbone for use.

7 Claims, 4 Drawing Sheets

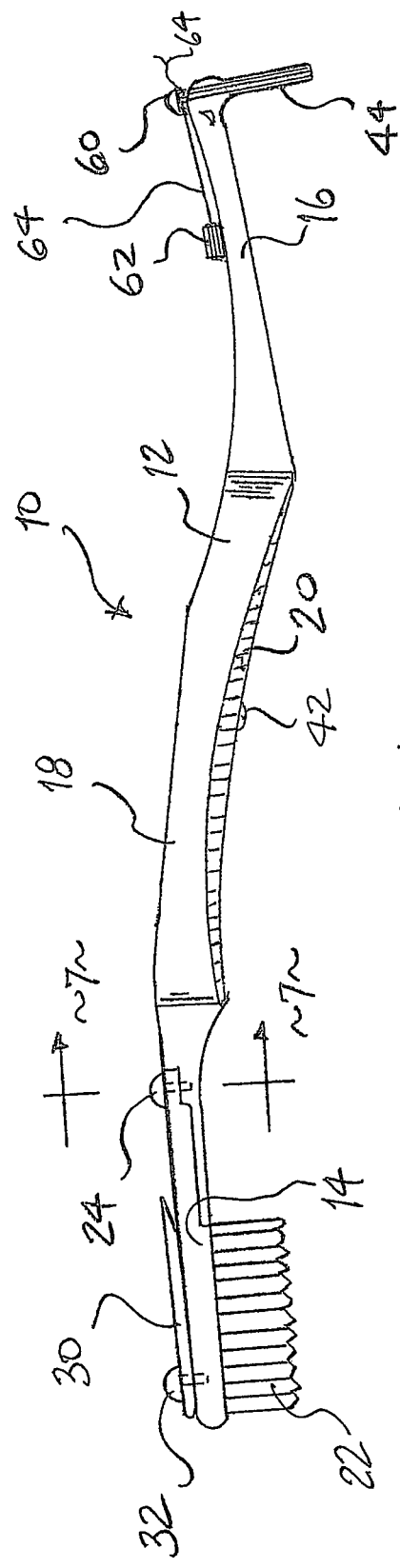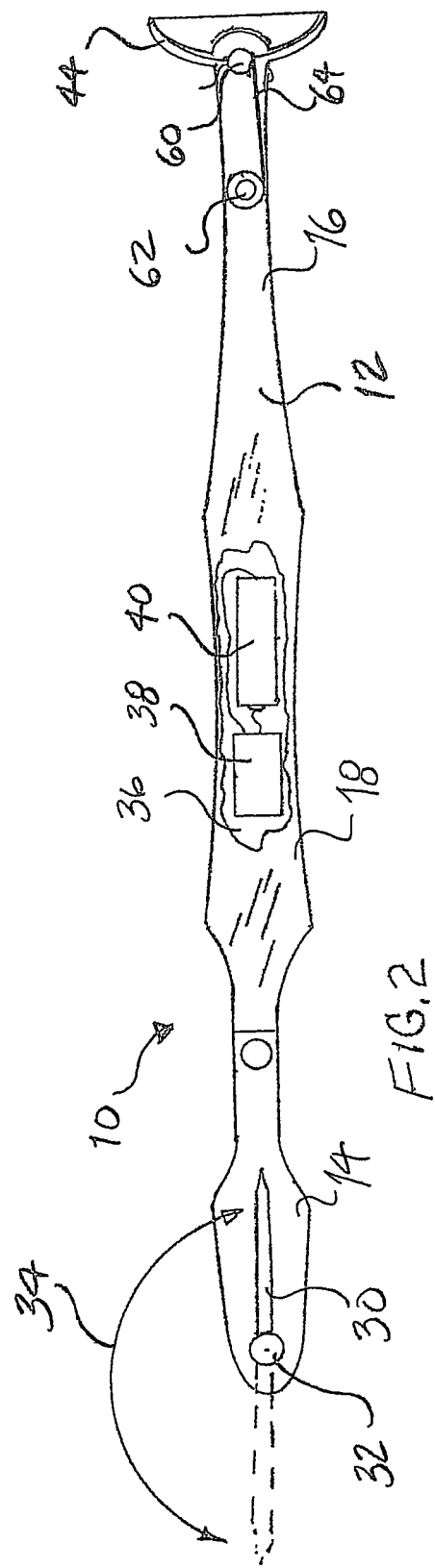
FIG. 1
FIG. 2

DENTAL CARE DEVICE

CROSS-REFERENCES TO RELATED APPLICATIONS

The present application is a continuation-in-part of prior filed patent application Ser. No. 12/316,971, filed 17 Dec. 2008 now abandoned.

BACKGROUND OF THE INVENTION

The present invention relates to a novel and useful dental care device.

Many dental care devices have been proposed to allow a person to carry out dental hygiene procedures such as brushing of teeth and flossing between adjacent teeth.

In the past, dental hygiene devices have employed the combination of toothbrushes and dental floss holders. For example, United States Patent Application Publication 2003/0019503 describes a dental floss holder which allows the dispensing of dental floss and also includes a toothbrush on the opposite end of the handle.

United States Patent Application Publication 2004/0187887, DES 191,821, DES 283,761, and DES 290,312 show the combination of a toothbrush in a dental floss holder in the form of a fork opposite the brush along the shaft.

United States Patent Application Publication 2005/0211262 describes a floss holder in combination with a toothbrush in which the floss is dispensed from the inside of the legs of the fork to the exterior thereof.

U.S. Pat. No. 2,233,936 and DES 420,805 describe toothbrush and flosser combination in which the floss is extended from a spool on the toothbrush and held across the legs of a fork by a flange.

U.S. Pat. Nos. 1,537,853 and 2,113,439 teach dental cleaning devices in which a toothbrush is used in combination with a floss dispenser in the form of a fork that uses notches on the end of the fork to steady the floss material.

U.S. Pat. Nos. 2,517,806, 3,850,182, 4,016,891, and Patent Application Publication 2004/0040571 illustrate combined toothbrush and dental floss holders in which the dental floss is extended to a fork which includes an exterior groove to guide the floss to the spanning portion of the legs.

A dental care device which utilizes a toothbrush structure and a floss holder which is easy to use to be a notable advance in the field of the dental arts.

BRIEF SUMMARY OF THE INVENTION

In accordance with the present invention a novel and useful dental care device is herein provided.

The dental care device of the present invention employs a shaft having a proximal end portion, a distal end portion, and an intermediate portion therebetween.

A dental brush is located at the shaft distal end portion. A mechanism is also provided for allowing the replacement of the dental brush when it is worn.

The intermediate portion of the dental care device shaft may be formed with a chamber to hold a vibrator which augments the brushing action of the dental brush by the use of agitation. A Switch is also accessible at the intermediate portion to activate the vibrator.

Moreover, the dental care device of the present invention includes a wishbone support at the proximal end portion of the shaft. The wishbone support possesses an outer surface having a groove which extends along first and second legs of the wishbone. A movable post located on the wishbone is positioned to allow the turning of the dental floss therearound in order to tightened the same and allow the spanning of the dental floss between the first and second legs. A spool is conveniently located on the top surface of the shaft to allow direct feeding of the dental floss strand around the post and to the legs of the wishbone.

The wishbone legs may also include one of more picks that extend downwardly and maybe conveniently used to clean particulate matter from between the teeth of the user. Likewise, a pick is rotatably held to the toothbrush head to permit the user to operate the same as a dental pick without reversing the grip of the toothbrush following brushing.

It may be apparent that a novel and useful dental care device has been hereinabove described.

It is therefore an object of the present invention to provide a dental care device which allows the user to brush and to floss ones teeth without using separate implements.

Another object of the present invention is to provide a dental care device which is capable of holding a strand of dental floss payed out from a spool on the outside surface of the device.

A further object of the present invention is to provide a dental care device which includes a vibrator mechanism which provides cleaning motion to the bristles of the toothbrush and the same as being used to clean the teeth of the user.

Yet another object of the present invention is to provide a dental care device utilizing a toothbrush, a floss holder, and a vibrator in combination.

A further object of the present invention is to provide a dental care device utilizing a dental floss holder which is interchangeable on a toothbrush support.

The invention possesses other objects and advantages which will become apparent as the specification continues.

BRIEF DESCRIPTION OF THE SEVERAL VIEWS OF THE DRAWING

FIG. 1 is a side elevational view of the dental care device of the present invention.

FIG. 2 is a top plan view of the dental care device depicted in FIG. 1.

Figure 3:
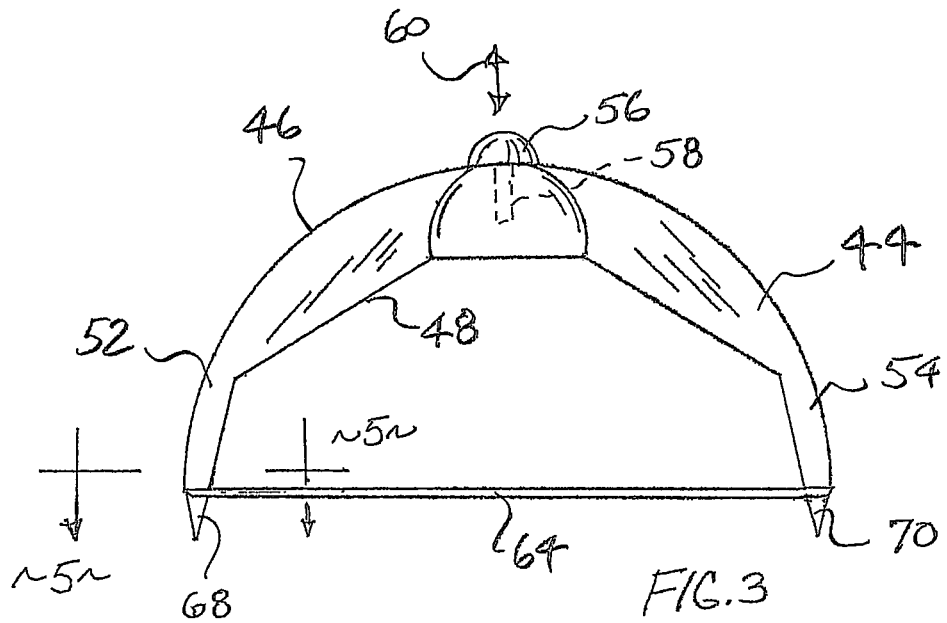
FIG. 3 is a rear elevational view of the wishbone support used to hold dental floss at the proximal end portion of the shaft.
Figure 4:
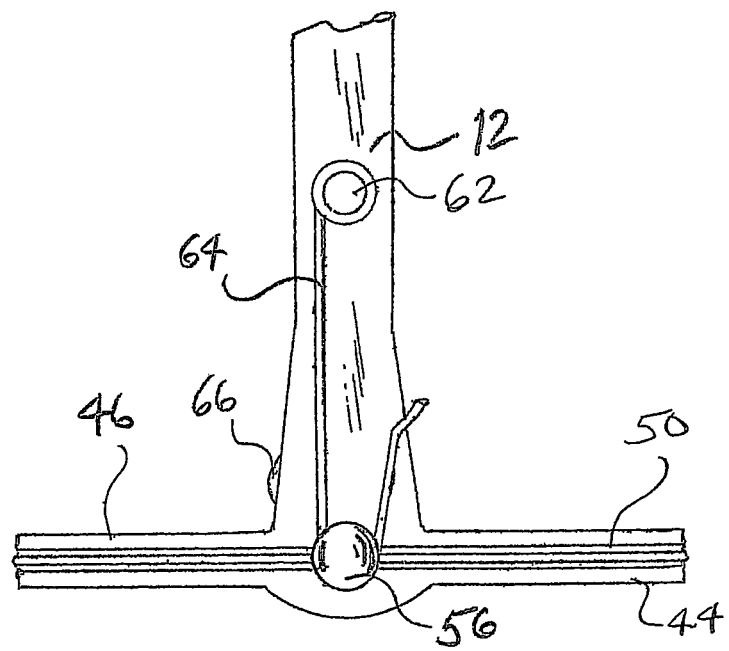
FIG. 4 is a top plan view of the wishbone support holding dental floss.

For a better understanding of the invention reference is made to the following detailed description of the preferred embodiments of the invention which should be taken in conjunction with the above described drawings.

DETAILED DESCRIPTION OF THE PREFERRED EMBODIMENTS OF THE INVENTION

Various aspects of the present invention will evolve from the following detailed description of the preferred embodiments thereof which should be referenced to the prior described drawings.

An embodiment of the invention is depicted as whole in the drawings by reference character 10. Device 10 includes a shaft 12 which may be constructed of any suitable rigid or semi-rigid material. Shaft 12 is generally formed with a distal end portion 14, proximal end portion 16, and an intermediate portion 18. In general, intermediate portion 18 is used to grip device 10 and gripping surface 20 aids in this endeavor, FIG. 1.

Figure 7:
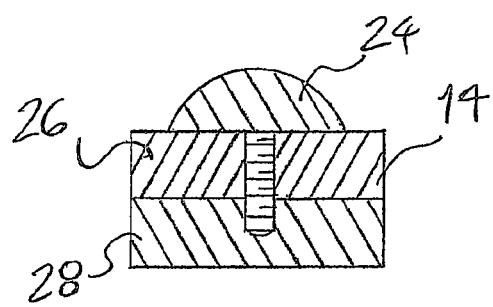
FIG. 7 is a sectional view taken along line 7-7 of FIG. 1.

Again, with reference to FIG. 1, it may be observed that distal end portion 14 of shaft 12 serves as the location for dental brush 22. Dental brush 22 is detachable from shaft 12 via a set screw 24 which holds ends 26 and 28 in overlying or overlapping relationship, FIGS. 1 and 7. Dental pick 30 is rotationally held to dental brush 22 by the use of pivot pin 32. As in depicted in FIGS. 2 and 8, dental pick 30 is capable of rotating outwardly into a position atop dental brush 22, to an orientation, as needed. Directional arrow 34 indicates such movements.

Referring now to FIG. 2, it may be observed that intermediate portion 18 of shaft 12 includes a chamber 36 which holds a vibrator 38 and a source of power 40 in the form of a battery. Button 42, FIG. 1 is capable of activating and de-activating vibrator 38. Vibrator 38 is positioned against shaft 12 to provide such vibratory motion to brush 22 as well as to other portions of device 10.

Figure 5:
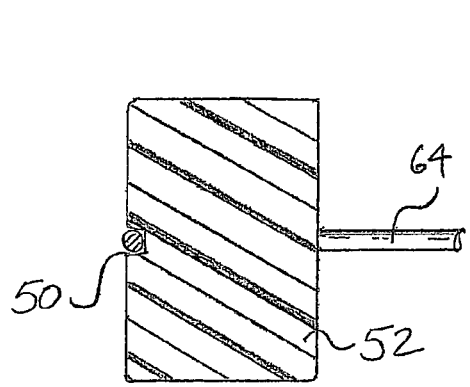
FIG. 5 is a sectional view taken along line 5-5 of FIG. 3.

Turning now to FIGS. 1, 2, 3, and 4, it may be seen that wishbone support is found at proximal portion 16 of shaft 12. Wishbone support 44 is fixed to the end of shaft 12 at proximal end portion 16 and possesses an outer surface 46 and an inner surface 48. A groove 50 is located along outer surface 46 and generally extends along legs 52 and 54 of wishbone support 44, FIGS. 4, 5, and 6. Post 56 fits within an opening 58 in wishbone support 44 and is movable upwardly and downwardly according to directional arrow 60, FIG. 3.

Spool 62 is found on proximal end portion 16 of shaft 18. Spool 62 is employed to hold a strand of dental floss 64 and to pay out or mete the same to post 56.

In any case, dental floss wrapped around post 56 travels along groove 50 and spans legs 52 and 54 as shown clearly in FIG. 3. Post 56, being moveable from opening 58, allows the capture of a portion of the strand of dental floss 64 and firmly holds the same when post 56 is pressed downwardly into wishbone support 44. A blade 66 attached to shaft 12, FIG. 4, allows the user to cut the bitter end of dental strand 64 after leading dental strand 64 from spool 62 and into contact with wishbone structure 44, heretofore described.

Figure 6:
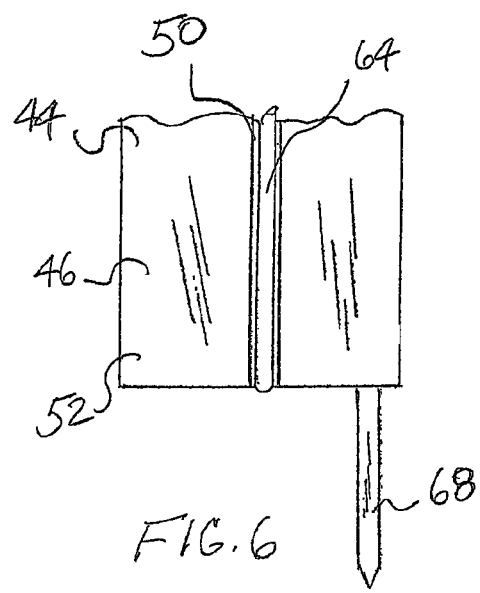
FIG. 6 is a side elevational view of the leg end portion depicted in FIG. 5.

With reference to FIGS. 3 and 6, it may be apparent that picks 68 and 70 are positioned at the ends of legs 52 and 54 of wishbone support 44. As is shown on FIG. 6, pick 68 does not interfere with strand 64 found in groove 50 of leg 52. The same structure applies to strands 64 relative to pick 70 and leg 54 of wishbone support 44. Picks 68 and 70 may take various shapes commensurate with use, i.e.: normal teeth, teeth having braces etc.

Figure 9:
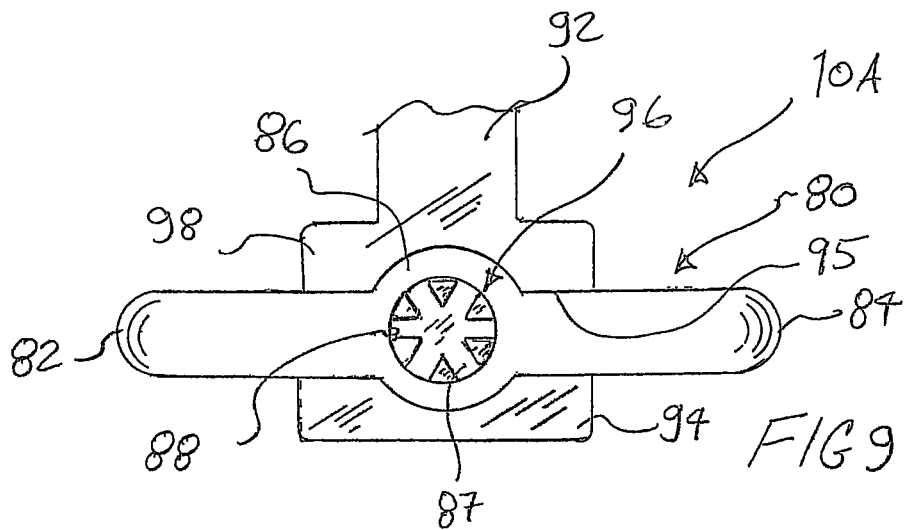
FIG. 9 is a top plan view of an alternate embodiment of the present invention depicting a snap-in dental floss holder.
Figure 10:
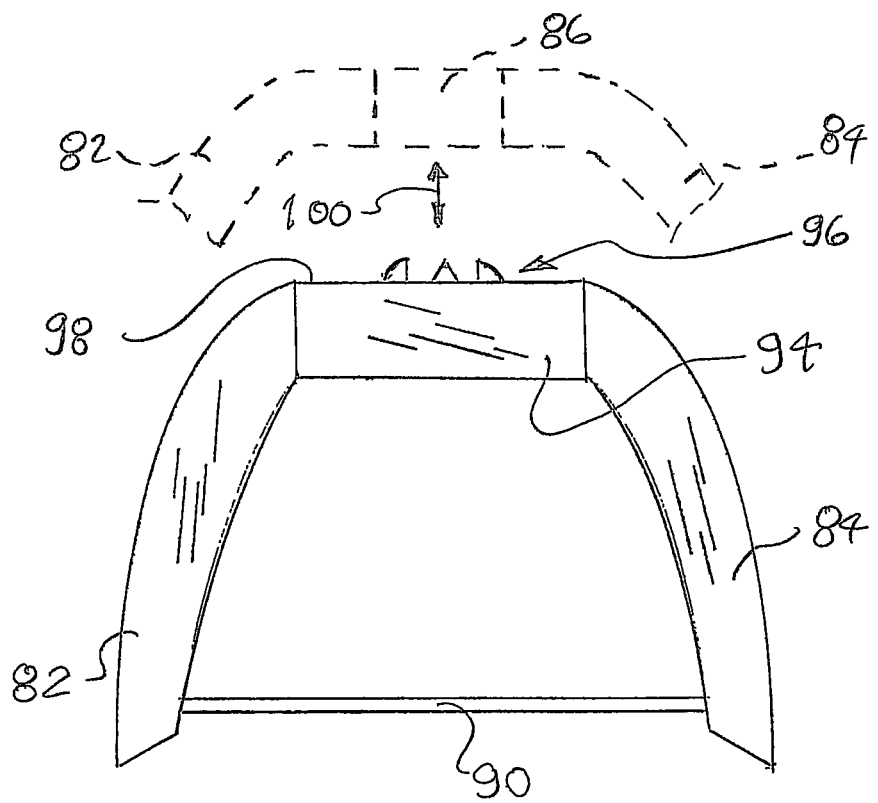
FIG. 10 is a rear elevational view of the embodiment shown in FIG. 9.

Turning now to FIGS. 9 and 10, it may be observed that another embodiment 10B of the device of the present invention is shown. Device 10B includes a floss holder 80 which is formed from a pair of legs 82 and 84 that are linked to one another by a intermediate portion 86. Intermediate portion 86 includes a circular aperture 87 having a circular aperture wall 88. Strand of floss 90 spans legs 82 and 84, FIGS. 9 and 10. A toothbrush handle 92, terminates which may include the features of shaft 12, in a rectangular solid end 94 analagores to proximal end 16 of shaft 12. End 94 possesses a plurality of flexible protrusions 96 extending from upper surface 98 thereof. End 94 also includes a channel 95 to fit floss holder 80. Intermediate portion 86 of floss holder 80, via circular aperture wall 88, engages plurality of protrusions 96 when intermediate portion 86 of floss holder 80 is pressed downwardly into channel 95, as shown in the positions depicted in FIGS. 9 and 10. FIG. 10 also illustrates, in phantom, the separation of floss holder 80 from channel 95 of rectangular solid end 94, connected to toothbrush handle 92, directional arrow 100.

Figure 8:
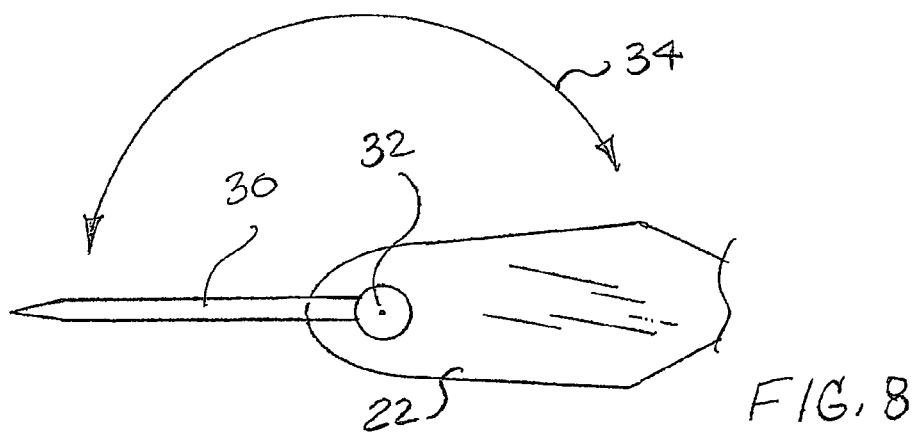
FIG. 8 is a top plan view showing the dental brush and rotatable pick, with the pick extended for use.

In operation, the user places brush head 22 on shaft 12 by the use of set screw 24. Brushing may take place with or without the use of vibrator 38 which is actuated by button 42 at the underside of intermediate portion 18 of shaft 12. Pick 30 may be employed by rotating the same outwardly from brush 22 about pivot pin 32. Directional arrow 34 on FIGS. 2 and 8 depicts such movement. Of course, pivot pin 32 may hold pick 30 in its desired position by frictional tightening. Strand of dental floss 64 is unwound from spool 62 and around post 60. From this point, dental floss strand 64 is passed along groove 50 found in wishbone structure outer surface 46, is extended across legs 52 and 54, in a spanning configuration, and continues along groove 50 back to post 56 where it is again, preferably, wrapped. Post 56 is slightly loosened in this configuration and, subsequently, pressed downwardly to frictionally hold the wrapped portion of dental strand 64 against wishbone structure 54. Thus, strand 64 is now tight between legs 52 and 54 and may be used thereby. Bitter end of strand 64 may be cut by the use of blade 66. When the user has employed strands 64, new floss maybe unwound from spool 62 and lead around post 56 through groove 50 and across legs 52 and 54 in the same manner. Picks 68 and 70 may be employed following flossing without reversing the grip on handle or shaft 12. The interchangeable floss holder 80 FIGS. 9 and 10, may be used with embodiment 10A of the device of the present invention. Floss holder 80 snaps in and out of channel 95 of end 94 by engagement of intermediate portion 86 with plurality of springy or flexible protrusions 96.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A dental care device utilizing a strand of dental floss, comprising:
   a. a shaft, said shaft having a proximal end portion, a distal end portion, and an intermediate portion between said proximal and distal end portions;
   b. a dental brush located at said shaft distal end;
   c. a wishbone support, said wishbone support being connected to said shaft proximal end portion, said wishbone support further including first and second legs and an intermediate portion, between said first and second legs forming a curved outer surface thereof, said first and second legs of said wishbone support each extending from said intermediate portion and terminating in free ends, said free end of said first legs being spaced from said free end of said second leg:
   d. a groove extending substantially continuously along said curved outer surface formed by said first and second legs; and said intermediate portion of said wishbone support:
   e. a cavity at said intermediate portion of said wishbone support, said cavity lying along said groove extending continuously along said curved outer surface formed by said first and second legs and said intermediate portion f. a post removably insertable into said cavity in said intermediate portion of said wishbone support, said post allowing the turning of the dental floss strand therearound and the capture of a portion of the dental floss strand when said post is pressed into said cavity at said intermediate portion of said wishbone; said groove completely holding the dental floss therewithin about said curved outer surface, between said post and said free ends of said first and second legs, said dental floss strand extending between the free ends of said first and second legs;

g. a spool of dental floss removably positioned on said proximal end portion of said shaft such that said spool is disposed along the exterior of said proximal end of said shaft and is employed to hold said dental floss to pay out said floss to said post, enabling said floss to wrap around said post and travel along said groove and span said first and second legs.

2. The device of claim 1 which additionally comprises one pick selectively extending from said first and second ends of the first and second legs.

3. The device of claim 1 in which said dental brush is removably held to said intermediate portion of said shaft.

4. The device of claim 1 which further comprises another pick rotatably attached to said distal end portion of said shaft.

5. The device of claim 1 which further comprises a vibrator positioned against said shaft.

6. The device of claim 1 in which said wishbone support is removably held to said shaft.

7. A dental care device utilizing a strand of dental floss, comprising:
   a. a shaft, said shaft having a proximal end portion, a distal end portion, and an intermediate portion between said proximal and distal end portions;
   b. a dental brush located at said shaft distal end and being removably held to said intermediate portion of said shaft;
   c. a wishbone support, said wishbone support being removably held to said shaft, said wishbone support further including first and second legs and an intermediate portion, between said first and second legs forming a curved outer surface thereof, said first and second legs of said wishbone support each extending from said intermediate portion and terminating in free ends, said free end of said first legs being spaced from said free end of said second leg:
   d. a groove extending substantially continuously along said curved outer surface formed by said first and second legs; and said intermediate portion of said wishbone support:
   e. a cavity at said intermediate portion of said wishbone support, said cavity lying along said groove extending continuously along said curved outer surface formed by said first and second legs and said intermediate portion
   f. a post removably insertable into said cavity in said intermediate portion of said wishbone support, said post allowing the turning of the dental floss strand therearound and the capture of a portion of the dental floss strand when said post is pressed into said cavity at said intermediate portion of said wishbone; said groove completely holding the dental floss therewithin about said curved outer surface, between said post and said free ends of said first and second legs, said dental floss strand extending between the free ends of said first and second legs;
   g. a spool of dental floss removably positioned on said proximal end portion of said shaft such that said spool is disposed along the exterior of said proximal end of said shaft when in use;
   h. a first pick selectively extending from said first and second ends of the first and second legs and a second pick rotatably attached to said distal end portion of said shaft;
   i. a vibrator positioned against said shaft.

\* \* \* \* \*